United States Patent [19]

Joyce et al.

[11] Patent Number: 5,047,343

[45] Date of Patent: Sep. 10, 1991

[54] MICROTUBER PROPAGATION OF POTATOES

[75] Inventors: Peter J. Joyce; Brent H. McCown, both of Madison, Wis.

[73] Assignee: Wisconsin Alumni Research Foundation, Madison, Wis.

[21] Appl. No.: 187,748

[22] Filed: Apr. 29, 1988

[51] Int. Cl.$^5$ .......................... C12N 5/04; A01H 4/00
[52] U.S. Cl. ........................ 435/240.45; 435/240.4; 435/240.54; 435/296; 47/58
[58] Field of Search ............ 47/58; 435/240.4, 240.45, 435/240.46, 240.54, 296

[56] References Cited

OTHER PUBLICATIONS

Stallknecht et al (1982) American Potato Journal 59:17-32.
"In vitro plant tissue culture and its agricultural application" 1986, Butterworths Chapter 11, pp. 113-122, A. J. Abott & A. R. Belcher: Potato Tuber formation in vitro *The whole document*.
Bioteknisk Laboratorium Nibe: "Fast reproduction of potatoes by BLN," ca. 1985 BLN Nibe. *p. 3, line 1-p. 5, line 13*.
"Potato physiology" 1985, Academic Press Chapter 15, pp. 503-577 P. J. Wang & C. Hy; Potato tissue culture and its applications in agriculture, *p. 511, lines 8-32; p. 539, line 7-p. 541, line 3, p. 544, line 4-p. 550, line 39*.
P. V. Ammirato et al-eds-"Handbook of plant cell culture" vol. 3, Crop species, Macmillan Publishing Co. 1984 New York, Chapter 11, pp. 291-328 S. A. Miller.
P. V. Ammirato in D. A. Evans et al., eds., (1983) Handbook of Plant Cell Culture, vol. 1, Macmillan Publ. Co., New York, p. 104.
Barker, W. G., "A Method for the in vitro culturing of Potato Tubers" (1953) Science 118:384-5.
Mingo-Castel, et al., "Studies on the Carbon Dioxide Promotion and Ethylene Inhibition of Tuberization in Potato Explants Cultured in Vitro", Plant Physiol. (1976) 57:480-485.
Mauk, Craighton S., et al., "Physiology of Tuberization in Solanum tuberosum L.", Plant Physiol (1978) 62, 438-442.
Palmer, C. E., et al., "Cytokinins and Tuber Initiation in the Potato Solanum tuberosum L.", Nature (1969) 221:279-280.
Stallknecht, G. F., "Coumarin-induced Tuber Formation on Excised Shoots of Solanum tuberosum L. Cultured in Vitro", Plant Physiol. (1972) 50:412-413.
Wang, Po-jen, et al., "In Vitro Mass Tuberization and Virus-Free Seed-Potato Production in Taiwan", American Potato Journal (1982) 59:33-37.
Wattimena, Gustaaf, et al., "Comparative Field Performance of Potatoes from Microculture", American Potato Journal (1983) 60:27-33.
Murashige, Toshio, et al., "A Revised Medium for Rapid Growth and Bio Assays with Tobacco Tissue Cultures", Physiol. Plant (1962) 15:473-497.
Bourque, et al., "Use of an In Vitro Tuberization System to Study Tuber Protein Gene Expression", In Vitro Cellular & Developmental Biology (1987) 23/5:381-386.
Rosell, G., F. G., et al., "In Vitro mass tuberisation as a contribution to potato micropropagation", Potato Research (1987) 30:111-116.
Ortiz-Montiel, G., et al., "Potato Minitubers: Technology Validation in Mexico", American Potato Journal (1987) 64:535-544.

(List continued on next page.)

Primary Examiner—Elizabeth C. Weimar
Assistant Examiner—Che Swyden Chereskin
Attorney, Agent, or Firm—Quarles & Brady

[57] ABSTRACT

The production of potatoes by growing a large number of independent shoot axes, each of which will form one or more microtubers, from a single microtuber is disclosed. This system has three interconnected stages: (1) the formation of a microtuber shoot complex by inducing shoot tip necrosis in the apical shoot; (2) the elongation of the resulting multiple shoot axes, and (3) the tuberization of the multiple shoot axes.

19 Claims, 1 Drawing Sheet

OTHER PUBLICATIONS

Slimmon, T., et al., *American Potato Journal* 64:458.

Hussey, G., et al., "Factors Affecting the Formation of In Vitro Tubers of Potato" (*Solanum tuberosum L.*), *Annals of Botany* (1984) 53:565-578.

Estrada, Rolando, et al., "Induction of in vitro in a broad range of potato genotypes", *Plant Cell, Tissue and Organ Culture* (1986) 7:3-10.

Sha, Liu, et al., "Occurrence and Cause of Shoot-tip Necrosis in Shoot Cultures", *J. Amer. Soc. Hort. Sci.* (1985) 110(5):631-634.

McCown, B. H., et al., "Field Performance of Micropropagated Potato Plants", *Biotechnology in Agriculture and Forestry* (1987) pp. 80-88.

McCown, Brent H., et al., "Nodule Culture: A Developmental Pathway with High Potential Metabolite Production from Woody Plants", *Genetics Manipulation of Woody Plants* (1988) pp. 149-166.

Dodds, John H., "Tissue Culture Technology: Practical Application of Sophisticated Methods", *American Potato Journal* (1988) 65:167-180.

MICROTUBER PROPAGATION OF POTATOES

FIELD OF THE INVENTION

The present invention relates generally to the production of potatoes and particularly to the use of microtubers in the production of potatoes. The present invention is specifically related to inducing a high rate of microtuber shoot formation, wherein each shoot will form a new tuber.

BACKGROUND OF THE INVENTION

The potato is one of the world's most economically important agricultural crop plants. A member of the Solanaceae family, potatoes are conventionally propagated clonally by subdividing tubers, i.e., the underground stems of the plant, into sections which are then planted.

The potato is a premier example of a crop where the control of diseases in the propagation phase is essential for consistent and high yields. The vigor and value of the crop depends in large part on maintaining the source tubers as virus and disease-free as possible. One way of achieving this goal is to produce the certified potato stocks in disease-free areas. However, such environments are not always available.

An alternative to the use of normal tubers for cloning potatoes for production is the micropropagation of microtubers, which are produced in completely disease-free environments. Microtubers are small in vitro produced tubers that are usually about the size of a pea. They are produced in sterile culture under controlled conditions.

Microtubers were first reported in the scientific literature by Barker (1953) *Science* 118:384-5. Until recently, the expense involved in the production of microtubers prevented the commercial exploitation of microtubers in the potato crop industry. As a result, microtubers were used primarily as a physiological tool to investigate the process of tuberization. Mingo-Castel, et al. (1976, *Plant Physiol.* 57:480-485) reported on the effects of carbon dioxide promotion and ethylene inhibition on the tuberization of potato explants cultured in vitro. Mauk and Langille (1978, *Plant Physiol.* 62:438-442) reported on the influence of temperature and photoperiod on the incidence and changes in a cytokinin in a potato plant tissue, and the effect of the cytokinin on in vitro tuberization. Palmer and Smith (1969, *Nature* 221:279-280) and Stallknecht (1972 *Plant Physiol.* 50:412-413) also reported on the effects of cytokinins and coumarin on in vitro tuberization of potato plants.

Wang and Hu (1982, *American Potato Journal* 59:33-37) were the first to report on the use of microtubers for the production of potatoes in the field. Subsequently, Wattimena, et al. (1983, *American Potato Journal* 60:27-33) compared the plant growth, the yield, and the tuber quality of two cultivars of potatoes grown from transplants generated from microcuttings or microtubers with potatoes grown from seed tubers. Both studies used (1) stem cuttings as the explant source for creating microtubers in vitro, (2) Murashige and Skoog (MS) mineral salt medium (Murashige and Skoog, 1962, *Physiol. Plant* 15:473-497), (3) high sucrose levels (6-8%), (4) low temperatures (15° C.-20° C.), and (5) a synthetic cytokinin to induce tuberization. The procedures differed significantly in the tuberization photoperiod, the method of multiplication, and agitation.

Subsequent publications have been based on both the stationary system (Bourque, et al., 1987, *In Vitro Cellular & Developmental Biology*, 23/5:381-386; Rosell, et al. 1987, *Potato Research* 30:111-116; Ortiz-Montiel, et al. 1987, *American Potato Journal*, 64:535-544; Slimmon and Souza-Machada, 1987, *American Potato Journal*, 64:458, and Hussey and Stacey, 1984, *Annals. of Botany*, 53:565-578) varying only in synthetic hormones, the photoperiod and the temperature; and the shaker system (Estrada, et al., 1986, *Plant Cell, Tissue and Organ Culture*, 7:3-10) where chlorocholine chloride was used in addition to benzyl amino purine (BA) for inducing tuberization.

As mentioned above, the commercial use of microtubers has been limited by the high cost of producing microtubers. This cost is in large part determined by the high input of labor necessary to produce microtubers based on the methods reported above. The labor demands are great because while every node of an in vitro grown shoot has the theoretical potential to form a microtuber, in general, only one microtuber will form on a multi-node shoot axis. Thus, in order to achieve a high rate of tuber formation, the nodes have to be separated from each other by manual manipulation, thus requiring a significant input (i.e., cutting and culturing) for each shoot to culture each microtuber.

An alternative approach to achieving high tuber numbers is the production of a large number of independently-growing shoot axes, each of which will form one or more microtubers. However, this approach has not heretofore been successful on potatoes since the commonly-used hormonal stimulants, such as cytokinins, for shoot multiplication are not particularly effective for potato shoot cultures grown under standard conditions.

SUMMARY OF THE INVENTION

It is therefore an object of the present invention to provide a novel and commercially-applicable method of increasing the number of potato shoots which will subsequently lead to microtuber formation.

It is further an object of the present invention to provide a method for inducing a high rate of microtuber formation from a potato shoot in in vitro culture.

These objects and others are met by the present invention which describes a method of inducing a high rate of microtuber formation beginning from a single potato microtuber. The method includes inducing a multiple shoot complex formation from the single shoot or shoots produced from the microtuber by the induction of shoot-tip necrosis on the growing shoot. By shoot-tip necrosis, it is meant that the condition of the tip of the potato shoot ceases to grow and dies, encouraging axillary branching and formation of a complex of subsidiary shoots. The modified shoot complex is then placed in a growth environment under conditions suitable for increasing the length of the shoot and allowing a separate root structure for each subsidiary shoot. The shoot complex is then placed under conditions suitable for allowing the tuberization of the shoots. The multiple shoot complex initially formed from one microtuber will then produce a multitude of microtubers.

The present invention is also directed to a microtuber-shoot complex produced by the above-described process.

Because the economical use of the potato transplant depends in large part on the number of times that the transplant must be handled, the method of the present invention is advantageous due to its low labor requirements. For example, only one manual manipulation of the plant tissue is required, i.e., at harvest. Further, no manual separation of the tuberization centers is necessary. Further still, any changing of the liquid media between the above-described steps can be easily and readily achieved by automated techniques as required.

DETAILED DESCRIPTION OF THE INVENTION

Figure 1:
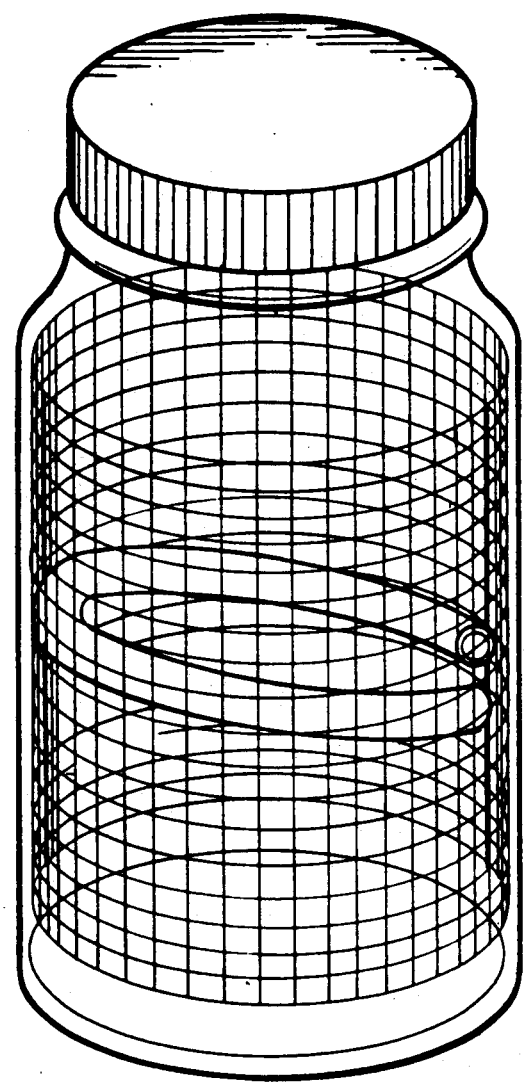

The microtuber multiplication system of the present invention has three interconnected stages: (1) the formation of the microtuber-shoot complex; (2) the elongation of the shoot axes; and (3) the tuberization of the shoot axes.

FORMATION OF MICROTUBER-SHOOT COMPLEX

In this stage, initial shoot axes are initiated from previously developed "seed" microtubers. The initial source explant is preferably a preselected sterile microtuber, grown in a dark, sterile environment, that has clearly broken dormancy and has visible sprouting. These shoots are more responsive to subsequent in vitro manipulations than, for example, shoot-culture derived shoots. The sterile microtubers have been generally stored at temperatures of about 5° C. in the dark for approximately 24 to 36 weeks.

The initial source shoots which are emerging from the microtuber explants are induced to extensively branch and form a mass of short shoot "initials", thus providing the basis for multiplication of the propagules. To achieve this formation, the microtubers are placed in an environment and nutrient medium which supports potato shoot growth. One suitable nutrient medium is a Murashige and Skoog (MS) (supra) mineral salt medium supplemented with vitamins, 3% (w/w) sucrose and 1.5 g/L gel rite. Cytokinins may optionally be added to the medium in order to enhance development of the shoots. Cytokinins, i.e., thidiazuron, are added at a concentration of approximately 1.0 micromolar (uM). Suitable examples of cytokinins which may be added to the nutrient medium are benzyl adenine (BA) or thidiazuron (TDZ). Preferably, the medium contains no or, at the very most, low levels of calcium.

The microtuber is allowed to grow at a temperature of between 20° and 25° C. (preferably 22° C.) in continuous light at 20–40 microEinsteins ($\mu$Ein sec$^{-1}$) of fluorescent light. The longer the conditions are kept under these conditions, the more shoot axes will be formed.

A preferred example of the nutrient medium for use on "Red Pontiac" microtubers is a MS medium which does not contain any levels of calcium, but contains 1.0 uM TDZ. The microtubers are allowed to grow at a temperature of 22° C. and under constant 20–40 microEinsteins fluorescent light.

It is within the scope of the present invention to allow the shoot axes to multiply by stimulating them with only cytokinins and the above-described medium with normal calcium levels; however, the rate of multiplication may be lower and the uniformity of shoot multiplication less. Generally, the microtuber shoot complex formation increases by the induction of shoot tip necrosis at low calcium levels. Maximum shoot axis stimulation is achieved with low calcium in combination with the cytokinin TDZ.

The basis of the shoot axis multiplication is in the injury to the shoot tip, i.e., shoot tip necrosis, which releases axillary buds from apical dominance. Sha, et al. (1985) *J. Amer. Soc. Hort. Sci.* 110(5):631–634. Under an in vitro environment, multiple shoot axes formed by the growth of these axillaries. The axillary or subsidiary shoots may be similarly effected and branch heavily, which further increases the number of shoot axes formed. This mass of short shoot axes with the accompanying mother microtuber is termed "microtuber-shoot complex".

The use of cytokinins in microtuber formation has been extensively studied. Cytokinins have been found to either act cooperatively to amplify the effects of a low calcium media, or independently to stimulate axillary branching of shoots emerging from the microtubers. This latter is a unique response for potatoes and differentiates microtuber-derived shoots from the more commonly used shoot cultures, where cytokinins are not particularly effective in stimulating axillary-based shoot multiplication.

ELONGATION OF THE SHOOT AXES

Each of the shoots of the newly-formed microtuber-shoot complex is not allowed to develop into an independent axis. The shoot complex is thus preferably transferred to a medium and environment which promotes the rapid growth of the potato shoots. This transfer may be accomplished by physically transferring the microtuber-shoot complex to a different culture vessel or most simply by changing the medium in the vessel. Although other methods are known to the art, such as a stationary bottle and a shaker bottle, the preferred environment is a roller bottle, also known to the art for providing a growth environment for other types of cell cultures. Roller bottles are rolled at a slow rate, i.e., $\frac{1}{2}$ revolutions per minute (rpm), so that a film of a growth medium is constantly maintained on the surface of the bottle. This process allows for the complete bathing of the developing shoots in the liquid medium while maintaining adequate gas exchange and nutrition. Further, the bathing of the shoots in the medium facilitates the subsequent tuberization during the next stage. The developing shoots are kept close to the sides of the bottle by the insertion of a coarse plastic mesh into which the shoots grow. The plastic mesh is preferably positioned as a liner on the interior of the roller bottle. This may be done by inserting a pliable plastic insert inside of the mesh placed in urn inside the bottle to hold the mesh against the inside of the bottle, as shown in the attached drawing figure. As the bottle turns, the microtubers are alternately immersed in medium and air. This prevents the shoot from having an orientation bias and also bathes the entire shoot in the medium.

The preferred environment is a liquid consisting of MS mineral salt medium supplemented with 3% (w/w) sucrose at a temperature of about 22° C. The shoot complex is kept in the dark during the development stage.

The process continues until the individual shoots are at least two centimeters (cm) in length. Further, the individual shoots may have independently derived roots even though they may still be attached to the original microtuber shoot axis and thus the mother microtuber. The entire process takes approximately two weeks.

The first week of the elongation stage may be benefited by the addition of cytokinins to the medium if the microtuber-shoot complex formation stage used no cytokinins in the process.

TUBERIZATION STAGE

The tuberization stage is that stage when numerous shoot axes have developed to a point where they become physiologically independent of each other while still being continuously and totally bathed in a growth medium. The elongated shoots emerging from the shoot complex are tuberized by one of the known in vitro tuberization procedures. A routine including a growth medium of MS mineral salts supplemented with 8% w/w sucrose and 3.2 uM cycocel in roller bottles at a temperature of 15° C. will induce microtubers in "Red Pontiac" within about two weeks. The microtubers will reach convenient harvest size in one to two months. The tuberization procedure is also well adapted to be used with the roller bottles.

Thus the method of the present invention utilizes three basic steps. First, culturing a shoot from a microtuber and then inducing shoot tip necrosis in the apical shoot, resulting in a proliferation of axillary or subsidiary shoots. Secondly, culturing the microtuber shoot complex thus produced to elongate the multiple shoot axes. Thirdly, inducing microtuber formation from the multiple shoots. The result is that the original "seed" microtuber is multiplied by the procedure resulting in up to ten or more daughter microtubers from the original one. Because the steps in the procedure involve simply changing media and environment conditions such as lighting and temperature, the process is well adapted for automated use. No human manipulation of the shoots or the culture need be required between inserting the original microtuber and removing the multiple microtuber mass for harvest. Thus the multiplication of microtubers for potential commercial use in the creation of aseptic microtubers for cultivation becomes practical.

The following examples are illustrative of the process of the present invention and show two examples of the microtuber multiplication system with two different potato cultivars.

Examples

EXAMPLE 1

Sterile "Red Pontiac" microtubers were stored in a stationary storage container in air in the absence of any growth medium or sucrose, and grown at 5° C. in the dark. After approximately six months the sterile microtubers were harvested and nine microtubers, which had clearly broken dormancy as evidenced by visible etiological sprouts, were utilized in the example.

The sprouts were sterilized in a 15% liquid bleach solution at room temperature, and rinsed twice with sterile distilled water. The surface disinfected microtubers were then transferred to a sterile growth medium consisting of MS medium supplemented with 3% (w/w) sucrose. No cytokinins were used. The medium contained no calcium. The microtubers were kept in this growth medium without agitation at a temperature of 22° C. under constant 20-40 $\mu$Ein sec$^{-1}$ light for approximately 7½ weeks to allow multiplication of the shoot axes on the developing microtuber shoot complex.

After the formation of the microtuber shoot complex, the complex was transferred to a MS growth medium with normal calcium chloride, 3% (w/w) sucrose and 1.0 uM thidiazuron, and incubated in the dark at 22° C. in a roller bottle rotating at ½ RPM for two weeks. After the two week period, the growth medium was replaced with fresh MS growth medium again containing calcium chloride, but omitting thidiazuron. The microtuber shoot complex was incubated for an additional week under the aforementioned conditions. By this time, the shoot axes of the microtuber shoot complex were at least two centimeters long and ready for tuberization.

The tuberization process used consisted of replacing the spent growth medium with fresh MS growth medium supplemented with 8% (w/w) sucrose, 170 uM coumarin and 3.16 uM cycocel. The microtuber shoot complex was then incubated in the dark at 15° C. in a roller bottle constantly rotating at ½ RPM. After two weeks, the growth medium was replaced with fresh MS growth medium supplemented with 4% sucrose, but no hormones. Approximately 2½ weeks later, the tubers reached a size convenient for harvesting.

The effect of Experiment 1 resulted in an average multiplication of 4.78 microtubers per tuber for each of the nine sterile microtubers initially processed in this experiment. Tuber multiplication for the nine replicates ranged from 1 to 11 fold.

EXAMPLE 2

Example 2 was conducted using "Superior" microtubers in place of "Red Pontiac" microtubers. The experimental procedure was similar to the same as that conducted in Experiment 1 with the following exceptions. Three sterilized and washed microtubers were transferred directly to a sterile growth medium consisting of the MS without calcium growth medium supplemented with 3% (w/w) sucrose and 1.0 uM thidiazuron, and incubated at 22° C. in the light for approximately ten weeks. The microtuber shoot complex was then transferred to a fresh MS growth medium supplemented with 3% (w/w) sucrose, but no hormones, and incubated in a roller bottle rotating at ½ RPM at 22° C. in the dark. After approximately two weeks, the growth medium was replaced with fresh MS growth medium supplemented with 8% (w/w) sucrose and 3.16 uM cycocel, and incubated in the dark at 15° C. under roller bottle conditions. Approximately four weeks later the tubers were harvested for observation.

The results of three replications of "Superior" sterile microtubers show a 2, 4 and 5 fold multiplication of tubers on the original microtubers.

It is understood that the invention is not confined to the particular construction and arrangement herein described, but embraces such modified forms thereof as come within the scope of the following claims.

What is claimed is:

1. A method of inducing tuber formation at a rate of more than two microtubers from a single potato microtuber explant comprising:
   (a) culturing a potato microtuber in vitro so that a shoot is formed therefrom;
   (b) inducing a microtuber-shoot complex formation containing multiple independently-growing shoot axes by culturing the microtuber in a medium sufficiently low in calcium so as to induce shoot-tip necrosis on the shoot growing from the microtuber;

(c) placing the microtuber-shoot complex in a growth medium under conditions suitable for increasing the length of the shoot axes and creating a root structure for the shoot axes; and (d) placing the microtuber shoot complex under conditions for encouraging the tuberization of the shoots so that multiple microtubers are formed on the independently-growing shoots.

2. The method of claim 1 wherein the potato microtuber is a sterile microtuber which has broken dormancy and is sprouting.

3. The method of claim 1 wherein the potato microtuber has been previously stored at a temperature of about 5° C. in the dark for from 24 to 36 weeks.

4. The method of claim 1 wherein the potato microtuber is from potatoes selected from the group consisting of Red Pontiac and Superior cultivars.

5. The method of claim 1 wherein the microtuber shoot complex is formed in Step (b) in the absence of calcium.

6. The method of claim 1 wherein the medium in Step (b) includes cytokinins to enhance development.

7. The method of claim 6 wherein the cytokinins are selected from the group consisting of benzyl adenine and thidiazuron.

8. The method of claim 1 wherein the conditions of Step (c) include a growth medium comprising Murashige and Skoog mineral salts supplemented with 3% (w/w) sucrose.

9. The method of claim 8 wherein the microtuber shoot formation is incubated at 22° C. in the dark under conditions allowing complete bathing of developing shoots in the growth medium and maintenance of adequate gas exchange and nutrition.

10. The method of claim 9 wherein the growth environment includes a roller bottle rotating at approximately ½ RPM in which the microtuber shoot complex is grown.

11. The method of claim 10 wherein the roller bottle includes material designed to keep the shoot axes close to the sides of the bottle.

12. The method of claim 11 wherein the material is plastic mesh.

13. The method of claim 1 wherein the length of time for inducing microtuber-shoot complex formation is approximately two weeks.

14. The method of claim 1 wherein the process of Step (b) is conducted in the absence of cytokinins and the process of Step (c) is conducted in the presence of cytokinins.

15. The method of claim 1 wherein the conditions of Step (d) include a growth medium comprising Murashige and Skoog mineral salts supplemented with 8% (w/w) sucrose and approximately 3.2 uM cycocel.

16. The method of claim 15 wherein the microtuber shoot formation is incubated at 15° C. in the dark in roller bottles rotating at approximately ½ RPM.

17. The method of claim 1 further comprising harvesting the microtubers from the microtuber shoot complex after the completion of Step (d).

18. A microtuber shoot complex having more than two microtubers produced by the process of claim 1.

19. A potato microtuber-shoot complex in vitro comprising;
a seed microtuber;
a plurality of axillary shoots originating from and connected to the seed microtuber, the axillary shoots having root formation; and
a daughter microtuber formed on at least two of the axillary shoots.

* * * * *